United States Patent [19]

Shortt

[11] Patent Number: 4,654,430
[45] Date of Patent: Mar. 31, 1987

[54] S-PROPARGYL TRITHIOPHOSPHONATE INSECTICIDES

[75] Inventor: Alexandra B. Shortt, Houston, Tex.

[73] Assignee: Stauffer Chemical Company, Westport, Conn.

[21] Appl. No.: 866,847

[22] Filed: May 27, 1986

Related U.S. Application Data

[62] Division of Ser. No. 685,581, Dec. 24, 1984, Pat. No. 4,614,735.

[51] Int. Cl.$^4$ .............................................. C07F 9/40
[52] U.S. Cl. .................................................... 558/217
[58] Field of Search ......................................... 558/217

[56] References Cited

U.S. PATENT DOCUMENTS 3,065,125  11/1962  Newallis et al. ..................... 558/217
3,261,743  7/1966  Wilson, Jr. ............................ 514/135
3,890,410  6/1975  Gutman ................................ 558/217

OTHER PUBLICATIONS

Abstract of SU 948107, 08/1983, from Heteroorganic Compounds A.S.

*Primary Examiner*—Anton H. Sutto
*Attorney, Agent, or Firm*—Joel G. Ackerman

[57] ABSTRACT

Compounds having the formula

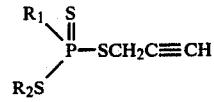

in which $R_1$ is methyl or ethyl and $R_2$ is ethyl or a $C_3$–$C_5$ branched alkyl group other than, 1,2-dimethylpropyl, are effective soil insecticides.

3 Claims, No Drawings

S-PROPARGYL TRITHIOPHOSPHONATE INSECTICIDES

This is a divisional of application Ser. No. 685,581, filed Dec. 24, 1984, now U.S. Pat. No. 4,614,735.

This invention relates to a series of trithiophosphonate insecticides, as defined below, which have been found particularly suitable for use in soil.

Various important crop plants are subject to attack by the larval stage of soil insects of a number of types, particularly of the genus Diabrotica, for example, the Northern corn rootworm (*Diabrotica longicornis*) and the Western corn rootworm (*Diabrotica virgifera*), which feed specifically on the root system of corn plants, the Southern corn rootworm (or spotted cucumber beetle) (*Diabrotica undecimpunctata*) which attacks peanut pods and also roots of corn plants, and the banded cucumber beetle (*Diabrotica balteata*), which attacks root systems of sweet potatoes. The larval stage of these insects attack or eat all of the smaller roots of infested plants and form tunnels in the larger roots, thereby weakening or destroying them. Corn plants growing in fields infested with the Northern or Western corn rootworm exhibit poor growth and may die, and the larger plants may fall down during or after a heavy rainfall or strong wind because of their weakened root system. Additionally, these soil insects seriously affect the quality of the harvested corn, particularly in the case of corn.

A number of other crops may have their root systems attacked by other insects in the soil. These insects include various maggots, wireworms, cutworks, larvae of various weevils or beetles, and white grubs.

In the past, the most common insecticides used to control such pests were halogenated hydrocarbons, particularly chlorinated hydrocarbons such as aldrin, dieldrin, heptachlor, DDT and BHC (benzene hexachloride). These compounds, however, leave heavy and persistent residues in the soil, which may remain in the soil for many years. Additionally, these halogenated hydrocarbons tend to be concentrated and stored for great lengths of time in animal tissues and thus in the food chains of animals or humans. They therefore have been either banned completely in developed countries or limited to a few specific uses.

While a number of organophosphorus derivatives have been found to be effective for control of insects on plant foliage, many such compounds have not been found satisfactory for use in the soil.

This invention is based on the determination, however, that a certain class of organophosphorus insecticides, some members of which are known to possess activity for foliar control of insects, possesses exceptionally good control of soil-borne insects, particularly of Diabrotica larvae, at low application rates. Additionally, some compounds of this type show good residual control.

Specifically, the compounds which are the subject of this invention have the general formula

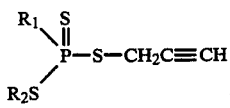

in which $R_1$ is methyl or ethyl and $R_2$ is ethyl or a branched $C_3$–$C_5$ alkyl group other than 1,2-dimethylpropyl. Preferably $R_1$ is ethyl and $R_2$ is a branched $C_4$ or $C_5$ alkyl group, as defined above.

Some compounds of this type are disclosed in U.S. Pat. No. 3,890,410 of Arnold D. Gutman. However, all insecticidal tests which are described in this patent are of the contact or leaf dip (foliar application) types; there is no information about activity as soil insecticides. Some compounds disclosed herein are new, notably those having doubly branched $C_5$ alkyl groups. Particularly active of the new compounds are those having 1,1-dimethylpropyl (tertiary amyl) and 2,2-dimethylpropyl (neopentyl) groups.

The compounds of the present invention may be prepared by the following two-step process.

In the first step, the appropriate alkyl thionophosphine sulfide is reacted with two equivalents of a desired mercaptan in the presence of a base to produce a thioic acid salt, according to the equation:

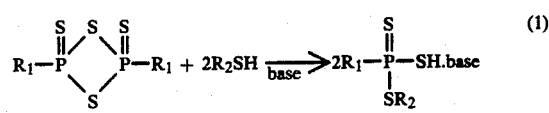

(1)

In the second step, the thioic acid salt is reacted with a propargyl halide:

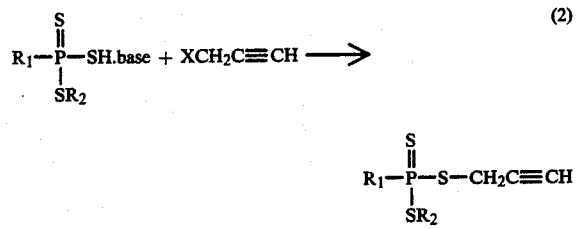

(2)

$R_1$ and $R_2$ are as defined above and X stands for halogen.

The starting material sulfides for Reaction 1 may be obtained for instance by the procedure described in P. E. Newallis et al., *Journal of Organic Chemistry*, 1962, Vol. 27, p. 3829.

Reaction 1 is advantageously carried out at a temperature of from about $-40°$ C. to about $150°$ C., preferably from about 0 to about $70°$ C., in an organic solvent in the presence of a base, preferably a tertiary amine. Suitable solvents include aromatic hydrocarbons such as benzene or toluene, ethers such as diethyl ether or tetrahydrofuran, and ketones such as acetone. A suitable tertiary amine is triethylamine. As the reaction is exothermic, the base is preferably added dropwise when operating on the laboratory scale. The product may be recovered by evaporating or distilling off the solvent.

Reaction 2 is conducted in an organic solvent such as that utilized in the first reaction, at a temperature of from about $20°$ C. to about $130°$ C., preferably from about $20°$ to about $70°$ C. The alkyl halide may be either a chloride or bromide. The product may be recovered by removing the precipitated salt, followed by evaporating or distilling off the solvent, and purification by chromatography.

The following represents an example of the preparation of one of the new compounds of this invention.

Preparation of S-propargyl,S-(1,1-dimethylpropyl)ethylphosphonotrithioate

(Compound 4 herein)

(a) To a slurry of 16.5 grams (g) of ethylthionophosphine sulfide in tetrahydrofuran, under nitrogen at room temperature, was added 13.8 g (0.133 mole) 1,1-dimethyl-1-propanethiol (tertiary amyl mercaptan). To this mixture was added 18.5 milliliters (ml) (0.133) triethylamine, dropwise. The mixture was stirred one hour at room temperature, then refluxed for ½ hour and stripped of solvent. There was obtained 30.1 g (87% of theoretical yield) of the triethylamine salt of S-(1,1-dimethylpropyl)ethylphosphonotrithioic acid).

(b) The triethylamine salt of step (a) (6.58 g, 0.02 mole) and propargyl bromide (2.97 g, 0.025 mole) were dissolved in tetrahydrofuran and the mixture refluxed for 3 hours, cooled, filtered, stripped, dissolved in ether and washed with ether and water, dried and again stripped. The residue was eluted with 2% ethyl acetate in hexane in a liquid chromatograph, yielding 2.52 g (47% of theoretical yield) of the desired product. Structure was confirmed by spectroscopic analyses.

The following Table I depicts representative compounds of this type which may be prepared as previously described. Structures of these compounds were confirmed by analyses as above.

TABLE I $$\begin{array}{c} R_1 \diagdown \overset{S}{\underset{\|}{P}} - S - CH_2C\equiv CH \\ R_2S \diagup \end{array}$$

| Compound Number | $R_1$ | $R_2$ | $n_D^{30}$ |
|---|---|---|---|
| 1 | $C_2H_5$ | 3-methylbutyl | 1.5628 |
| 2 | $CH_3$ | sec-$C_4H_9$ | 1.5815 |
| 3 | $C_2H_5$ | t-$C_4H_9$ | 1.5627 |
| 4 | $C_2H_5$ | 1,1-dimethylpropyl | 1.5878 |
| 5 | $C_2H_5$ | 2,2-dimethylpropyl | 1.5682 |
| 6 | $C_2H_5$ | sec-$C_4H_9$ | 1.5756 |
| 7 | $C_2H_5$ | $C_2H_5$ | 1.5987 |
| 8 | $C_2H_5$ | i-$C_3H_7$ | 1.5720 |

Insecticidal Evaluation Tests

The compounds in Table I above were tested for insecticidal activity using the following testing procedures. LD-50 values, based on the results of these tests, and/or calculated according to dosage-mortality curves, are expressed in Table II.

Housefly [*Musca domestica*]:

(a) Contact: Test compounds were diluted to acetone and aliquots pipetted onto the bottom of aluminum dishes. To insure even spreading of the chemical on the bottom of the dishes, 1 ml of acetone containing 0.01% peanut oil was also added to each dish. After all solvents had evaporated, the dishes were placed in circular cardboard cages containing 25 female houseflies, 1-2 days old. The cages were covered on the bottom with cellophane and on the top with tulle netting, and each contained a sugarwater saturated cotton plug for maintenance of the flies. Mortality was recorded after 48 hours. Test levels ranged from 100 µg/25 female houseflies downward. The LC-50 values are expressed below in Table II under the heading "HF-C", in terms of µg of the test compound per 25 female flies.

(b) Fumigant: Test compounds were diluted in acetone and aliquots pipetted onto 55 millimeter (mm) filter paper discs in the bottom of aluminum dishes. Immediately after the acetone had completely evaporated the dishes were placed in circular cardboard cages (volume-285 ml) containing 25 female houseflies. The cages were sealed on both ends with cellophane and each contained a sugar-water saturated cotton plug for maintenance of the flies. A piece of netting was placed over the aluminum dish in the cage in such a way that the flies were unable to come into direct contact with the chemically treated filter paper. Mortality was recorded after 48 hours. Test levels ranged from 100 µg/25 female houseflies downward. The LD-50 values are expressed in the following Table II under the heading "HF-F", in terms of µg of the test compound per 25 female houseflies per 285 ml volume of the test container.

Black Bean Aphid [*Aphis fabae* (Scop.)]:

Nasturtium plants (Tropaeolum sp.) approximately 5 cm tall, were transplanted into sandy loam soil in small cups and infested with 25-50 black bean aphids of mixed ages. Twenty-four hours later they were sprayed to the point of runoff with 50-50 acetone-water solutions of the test compounds. Treated plants were held in the greenhouse and mortality was recorded after 48 hours. Test concentrations ranged from 0.5% downward. The LD-50 values were expressed below in Table II under the heading "BA-C" in terms of percent of the test compound in the sprayed solution.

Tobacco Budworm [*Heliothis virescens* (Fabricius)]:

(a) Contact: Test compounds were diluted in a 50-50 acetone-water solution. Cotton (Gossypium sp.) cotyledons were immersed in the test solutions for 2-3 seconds and placed on a wire screen to dry. The dried leaves were placed in petri dishes containing a moistened piece of filter paper and infested with 5 second-instar tobacco budworm larvae. The dishes were placed in a high humidity chamber for 5 days, and percent mortality of the larvae recorded. Test concentrations ranged from 0.1% downward. The LD-50 values are expressed below in Table II under the heading "TBW-C" in terms of percent of the test compound in the solution.

(b) Eggs: Paper towel patches of 2-day old eggs of the tobacco budworm were dipped in acetone solutions of the test compounds and placed in petri dishes containing a portion of larval rearing medium. Treated eggs were maintained at 78° F. and mortality was recorded after all control eggs had hatched and the young larvae were feeding on the media. Test concentrations ranged from 0.1% downward. The LD-50 values are expressed below in Table II under the heading "TBW-E" in terms of percent of the test compound in the solution.

Beet Armyworm (*Spodoptera exigua*):

Test compounds were diluted in a 50-50 acetone-water solution. Young leaves of sugar beets (*Beta vulgaris*) were immersed in the test solutions for 2-3 seconds and placed on a wire screen to dry. The dried leaves were placed in petri dishes containing a moistened filter paper and infested with five second-instar beet armyworm larvae. The dishes were placed in a high humidity chamber. Mortality of the larvae was recorded five days later. Test concentrations ranged from 0.1% downward. The LD-50 values are expressed below in Table II under the heading "BAW" in terms of percent of the test compound in the solution.

Cabbage Looper [*Trichoplusia ni* (Hübner)]:

Test compounds were diluted in a 50-50 acetone-water solution. Cotyledons of hyzini squash (*Calabacita abobrinha*), approximately 1×1.5 inches, were immersed in the test solutions for 2-3 seconds and placed on a wire screen to dry. The dried leaves were placed in petri dishes containing a moistened piece of filter paper and infested with 5 second-instar cabbage looper larvae. The dishes were placed in a high humidity chamber. Mortality of the larvae was recorded 5 days later. Test concentrations ranged from 0.1% downward. The LD-50 values are expressed below in Table II under the heading "CL" in terms of percent of the test compound in the solution.

Western Spotted Cucumber Beetle Larvae [*Diabrotica undecimpunctata* (Mannherheim)]:

Ten grams of moist potting soil was placed in a plastic cup. Test compounds were dissolved in acetone or an other appropriate solvent. A 0.05 ml aliquot of the test sample, diluted to the desired concentration, was added to the soil. The cup was capped and the soil was mixed on a vortex mixer for approximately 15 seconds. An indentation was made on the surface of the soil and approximately 50 Diabrotica eggs were added. The eggs were covered with soil and maintained at room temperature (approximately 21° C.). Four days later a section of Romaine lettuce (*Latuca sativa*) leaf was placed in the treated cups. One week later the cups were examined for live larvae. Test concentrations ranged from 25 ppm downward. The LD-50 values are expressed below in Table II under the heading "Diabrotica" in terms of ppm of the test compound in the soil.

German Cockroach [*Blatella germanica* (Linn.)]:

Test compounds were diluted in a 50-50 acetone-water solution. Two ml of the solution was sprayed through a hand spray gun into circular cardboard cages containing 10 one-month old German cockroach nymphs. The test cages were covered on the bottom with cellophane and on the top with tulle netting. Percent mortality was recorded 4 days later. Test concentrations ranged from 0.1% downward. The LD-50 values are expressed below in Table II under the heading "GR" in terms of percent of the test compound in the sprayed solution.

Lygus Bug [*Lygus hesperus* (Knight)]:

Test compounds were diluted in a 50-50 acetone-water solution. Two ml of the solution was sprayed through a hand-spray gun into circular cardboard cages containing 1 green bean pod and 10 adult lygus bugs. The test cages were covered on the bottom with cellophane and on the top with tulle netting. Percent mortality was recorded 48 hours later. Test concentrations ranged from 0.5% downward. The LD-50 values are expressed below in Table II under the heading "LB" in terms of percent of the test compound in the sprayed solution.

Aster Leafhopper [*Macrosteles fascifrona* (Stal)]:

Oat seedlings (Avena sp.) were grown in a commercial potting soil in plastic cups. When the plants were approximately 10 cm tall they were thinned to 3 plants per cup and dipped for 2-3 seconds in 50-50 acetone-water solutions of the test compounds. When the plants had dried, a clear plastic tube was placed over them and the bottom end pressed into the cup. Ten aster leafhopper adults/nymphs were then placed in each tube and the tops of the tubes covered with white organdy cloth. Mortality counts were made after 48 hours. Test concentrations ranged from 0.5% downward. The LD-50 values are expressed below in Table II under the heading "LH" in terms of percent of the test compound in the solution.

Acaricidal Evaluation Test

The two-spotted mite (2SM) [*Tetranychus urticae* (Koch)] was employed in tests for miticides. The test procedure was as follows:

Pinto bean plants (Phaseolus sp.) approximately 10 cm tall, were transplanted into sandy loam soil in small cups and thoroughly infested with two-spotted mites of mixed ages and sexes. Twenty-four hours later the infested plants were inverted and dipped for 2-3 seconds in 50-50 acetone-water solutions of the test compounds. Treated plants were held in the greenhouse, and 7 days later mortality was determined for both adult mites and the nymphs hatching from eggs which were on the plants at the time of treatment. Test concentrations ranged from 0.05% downward. The LD-50 values are expressed below in Table II under the headings "2SM-A" (i.e., adults) and "2SM-E" (i.e. eggs) in terms of percent concentration of the test compound in the solution.

Systemic Evaluation Test

This test evaluates the root absorption and upward translocation of the candidate systemic compound. The two-spotted mite (2SM) [*Tetranychus urticae* (Koch)] and the bean aphid (BA) [*Aphis fabae* (Scop.)] were employed in the test for systemic activity. Tests were conducted as follows;

Two-Spotted Mite:

Test compounds were dissolved in acetone and aliquots diluted in 200 ml of water in glass bottles. Two pinto bean plants (Phaseolus sp.), with expanded primary leaves, were supported in each bottle by cotton plugs so that their roots and stems were immersed in the treated water. The plants were then infested with 75-100 two-spotted mites of various ages and sexes. One week later the mortality of the adult mites and nymphs was recorded. Test concentrations of the chemicals in the water ranged from 10 ppm downward. The LD-50 values are expressed in Table II under the heading "2-SM (S)" in terms of ppm of the test compound in the solution.

Black Bean Aphid [*Aphis fabae* (Scop.)]

Nasturtium plants (Tropaeolum sp.), approximately 5 cm tall, were transplanted into 400 grams of sandy loam soil in one pint containers. Test chemicals were dissolved in acetone and aliquots diluted in 50-60 ml of water. The treated water was poured onto the surface of the soil and allowed to thoroughly soak in. The treated plants were infested with 25-50 black bean aphids of mixed ages and held in the greenhouse. Mortality was recorded after three days. Test concentrations ranged from 10 ppm down to that at which 50% mortality occurs. The LD-50 values are expressed in Table II under the heading "BA(S)" in terms of ppm of the test compound in the soil.

TABLE II

| Cmpd. No. | HF, ug C | HF, ug F* | BA C, % | BA S, ppm | 2-SM A, % | 2-SM S, ppm | 2-SM E, % | (LD50) TBW, % C | (LD50) TBW, % E | BAW, % | CL, % | LH, % | GR, % | LB, % | Diabrotica, ppm (soil) |
|---|---|---|---|---|---|---|---|---|---|---|---|---|---|---|---|
| 1 | 20 | — | 0.008 | — | >0.05 | — | — | — | — | — | — | — | — | <0.05 | 6 |
| 2 | 20 | — | 0.003 | — | <0.05 | — | — | — | — | — | — | — | — | <0.05 | 0.9 |
| 3 | 30 | 54 | 0.05 | >10 | 0.01 | 6 | 0.05 | 0.03 | 0.007 | >0.1 | 0.008 | 0.05 | 0.03 | 0.03 | 0.75 |
| 4 | 7 | 21 | 0.002 | >10 | 0.003 | >10 | 0.03 | 0.02 | 0.003 | 0.009 | 0.002 | 0.05 | <0.1 | 0.02 | 0.75 |
| 5 | 7 | 8 | 0.001 | 6 | 0.05 | >10 | >0.05 | 0.005 | 0.001 | 0.006 | 0.003 | — | — | — | 0.75 |
| 6 | 30 | 7.5 | 0.006 | 6 | 0.05 | >10 | >0.05 | 0.006 | 0.002 | 0.006 | 0.003 | 0.006 | 0.03 | 0.008 | 2 |
| 7 | <100 | — | 0.05 | >10 | 0.05 | >10 | >0.05 | 0.08 | 0.03 | 0.03 | 0.03 | — | 0.075 | >0.05 | 0.3 |
| 8 | <100 | — | 0.05 | 10 | 0.03 | >10 | >0.05 | 0.03 | 0.02 | 0.05 | 0.003 | — | 0.09 | >0.05 | 0.75 |

KEY:
C = Contact test
E = Test on eggs
F = Fumigant test
A = Test on adults
S = Systemic test
*Per 285 ml volume container Black cutworm [*Agrotis ipsilon*]

Compounds 4 and 5 were tested for control of the black cutworm. The procedure was the same as that utilized for the cabbage lopper. Test concentrations ranged from 0.1% downward. LD-50 values, in terms of percent of the test compound in the solution, are reported below in Table III.

TABLE III

| (Black cutworm) | |
|---|---|
| Compound No. | LD$_{50}$, % |
| 4 | 0.03 |
| 5 | 0.002 |

A compound in which $R_1$ is ethyl and $R_2$ is 1,2-dimethylpropyl was also submitted to insecticidal evaluation. It demonstrated control of several insects at screening levels or below, but did not control Diabrotica at 25 ppm.

Soil Residual Control of Diabrotica

Test compounds showing good control of Diabrotica in the evaluation procedures were submitted for evaluation of residual control of this insect. Compounds 3 and 4 were evaluated at concentrations of 2 ppm in the soil. Other compounds were evaluated at concentrations of approximately twice the demonstrated LD-50 in the earlier tests.

Test compounds were incorporated into 200 g of soil at the indicated concentrations. The soils were maintained at a constant soil moisture in the greenhouse. At weekly intervals, 10-gram samples were taken and placed in a small cup. An indentation was made on the soil surface and approximately 50 Diabrotica eggs were added, covered with soil, and the cup covered. A piece of Romaine lettuce was added four days later. The cups were examined for live larvae one week later.

Table IV indicates the number of weeks of Diabrotica control (50% mortality) exhibited by test compounds at the indicated concentrations.

TABLE IV

| (Residual Control) | | |
|---|---|---|
| Compound Number | ppm | Control of Diabrotica Weeks |
| 3 | 2 | 1 |
| 4 | 2 | 8 |
| 5 | 1.5 | 3 |
| 7 | 0.6 | <2 |
| 8 | 1.5 | 3 |

In practice, a pure compound can be used as an insecticide. However, in general, the compounds are first formulated with one or more inert (i.e. non-chemically reactive, plant compatible or herbicidally inert) carriers or diluents suitable for insecticidal use, before being applied.

The compositions or formulations, including a compound as described herein, may take any one of a number of solid or liquid forms. Examples of solid forms are dusts, granules, tablets, powders and the like. Examples of liquid forms are emulsions, solutions, suspensions, flowables, emulsifiable concentrates and pastes. Such compositions may contain, in addition to the active compound or compounds, various carriers or diluents; surface-active agents (wetting agents, dispersing agents and/or emulsifying agents); solvents (water, or organic solvents such as aromatic solvents or chlorinated aliphatic solvents); adhesives; thickeners; binders; antifoaming agents; and other substances as mentioned herein. Solid carriers or diluents included in such compositions or formulations may include, for example, ground natural minerals such as kaolins, alumina, calcium carbonate, silica, kieselguhr, diatomaceous earth, pumice, clays, etc.; ground synthetic minerals such as various silicates and aluminosilicates and ground vegetable products such as bark, cornmeal, sawdust, cellulose powder and the like. Some sorptive minerals, especially clays, may cause decomposition of active substances over a period of time. In such compositions, a stabilizer, for example, a glycol, may therefore be necessary.

To manufacture solid compositions, the active substances are mixed with solid carriers or diluents such as those mentioned above and the mixture is ground to the appropriate size. Granules can be manufactured by dissolving an active compound in an organic solvent and applying the mixture, for example, by atomization, onto an absorptive granulated inert material, such as silica. Adhesives may be utilized to assist in the incorporation of the compound onto the solid particles.

Wettable powders and pastes are obtained by mixing and grinding an active compound with one or more dispersing agents and/or solid carriers or diluents. Also included may be wetting agents and/or dispersing agents, for example, lignins, methyl cellulose, naphthalenesulfonic acid derivatives, fatty alcohol sulfates and various types of alkali and alkaline earth metal salts of fatty acids.

Emulsifiable concentrates are generally obtained by dissolving the active compound in an organic solvent, for example, butanol, cyclohexanone, xylenes, or higher boiling aromatic hydrocarbons. To obtain suspensions or emulsions in water, wetting agents may also be added.

Flowables are prepared by mixing an active compound with one or more dispersing agents and/or solid additives, and a liquid (which may be water or an organic solvent) in which the active compound is relatively insoluble, and grinding the mixture.

Both liquid and solid compositions may be in microcapsule or encapsulated form, to permit release of the enclosed active compound at a controlled rate over a period of time. Liquid compositions of this type contain encapsulated droplets of approximately 1-50 microns in diameter, including the active compound and optionally a solvent. The encapsulating material is an inert porous membrane of a polymeric material.

Solid encapsulated compositions generally take the form of granules, in which the liquid containing the active component is trapped in the pores of the granular support by a porous polymeric membrane through which the active ingredient may migrate at a controlled rate, or which membrane breaks down at a controlled rate to permit escape of the active ingredient.

Typical encapsulating materials include natural and synthetic rubbers, cellulosic materials, styrene-butadiene copolymers, polyacrylonitriles, polyacrylates, polyamides, polyisocyanates, polyurethanes, mixed copolymers of the foregoing and starch xanthates.

It is possible to use highly connected liquid compositions containing up to about 95% by weight of the active compound, or even the 100% active compound alone, when applying the compound in the form of a finely divided liquid by use of various atomizing equipment, for example by airplane spraying techniques. For other purposes, however, the various types of compositions which can be utilized for these compounds will contain varying amounts of the compound according to the type of composition and the intended use.

In general, insecticidal compositions may contain from 5 to 95% of the active compound, more preferably from 10 to 85%. Some typical compositions will contain an active compound as follows: wettable powders: 25 to 80% active compound; oil suspensions, emulsions, solutions, flowables, and emulsifiable concentrates: 5 to 85% active compound; aqueous suspensions: 20 to 50% active compounds; dusts and powders: 5 to 20% active compound; granules and pellets: 5 to 20% active compound.

In addition to the active compound and the various agents utilized in preparing compositions and formulations mentioned, such compositions may also contain one or more other active compounds of the type mentioned herein as well as other active pesticidal agents, such as herbicides, fungicides, insecticides, acaricides, nematocides, bactericides, and plant growth regulators. Such compounds may also contain soil disinfectants or fumigants and may further contain fertilizers, thus making it possible to provide multi-purpose compositions containing one or more of the active compounds described herein as well as, optionally, other pesticides and also fertilizers, all intended and formulated for use at the same locus.

Control of insect pests is accomplished by applying a composition containing an insecticidally effective amount of an active compound as described herein to the insect, to a locus at which insecticidal control is desired, or to food sources (including seeds) on which the insects feed. For use in the last mentioned manner it is preferable to utilize a compound which is not volatile. Thus, control may be achieved by direct application of the active compounds to the insects and indirectly by application of the compounds to a locus to be protected (such as crop lands, grass ranges and forests), to a source of food for insects or to other insect habitats (for example, breeding or swarming areas). The rates of application of the active compound, and the concentration applied, will vary according to whether the compound or composition is being directly applied to the insect or indirectly, to a locus, food or habitat. In the latter case the rate of the application, depending on the nature of the insect or insects to be controlled, and the plant environment, will generally vary from about 0.01 to about 100 pounds per acre (about 0.012 to about 111 kg/ha).

It should be noted that the active compound need not be insecticidally active per se to effect insect control. The purposes of this invention are fully served if such compounds are rendered active by external influences, such as light or heat, or by some physiological action which occurs when the compound is ingested into the body of the insect.

Compositions containing one or more of the active compounds described, in an insecticidally effective amount, may be applied to the plant, locus or insect habitat in any conventional manner.

When used in connection with crop or other plant protection, application may be made in a preventive (i.e. before infestation) or eradicative manner (i.e., after infestation). Thus, powders and various liquid compositions containing the active compound can be applied by the use of power dusters, boom and hand sprayers and spray dusters, or applied from airplanes as dusts or sprays. When applied in the latter method they may be effective in very low dosages.

Compositions including active compounds may also be applied by addition to irrigation waters supplied to the field to be treated. This method of application permits penetration of the compounds into the soil as the water is absorbed therein.

Compositions including active compounds may additionally be used to protect plant seeds from being attacked by soil-borne insect pests after planting and during germination, by applying the composition to the seeds as a seed dressing. This is performed generally by mixing the seeds with an active composition in either liquid or solid form (preferably liquid) in a suitable mixing apparatus. Liquid compositions for this purpose may contain an adhesive or sticking agent, such as methyl cellulose, ethyl cellulose, etc., to assist the composition in adhering to the seed. If a solid composition is utilized for this purpose, an adhesive agent may be sprayed on the seeds during or after mixing.

For use as a soil insecticide, the active compound, or compositions containing it, may be mixed with the soil in any conventional manner, before, during or after planting of the plant seeds. Liquid compositions may be applied by spraying onto the surface or by incorporation in irrigation or sprayed water. Solid or liquid compositions containing an active compound may be incorporated into the soil prior to or during planting by discing, plowing or other mixing operations, in order to locate the active ingredient below the surface of the soil so as to be most effective in controlling undesirable larvae.

Some examples of compositions containing the active compounds of this invention are:

| Component | Weight % |
|---|---|
| Composition A: Granular Solid | |
| Compound 1. | 10 |
| calcined diatomaceous earth granules | 85 |
| triethylene glycol (stabilizer) | 5 |
| Total | 100% |
| Composition B: Wettable Powder | |
| Compound 2 | 80 |
| wetting agent (sodium dialkyl-naphthalene sulfonate) | 1 |
| dispersing agent (sodium lignosulfonate) | 4 |
| diluent (aluminum magnesium silicate) | 15 |
| Total | 100% |
| Composition C: Dilute Solution | |
| Compound 3 | 5 |
| solvent (xylene) | 95 |
| Total | 100% |
| Composition D: Emulsifiable Concentrate | |
| Compound 4 | 50 |
| Emulsifier (blend of metal sulfonates and polyoxyethylene ethers) | 10 |
| solvent (xylene) | 40 |
| Total | 100% |
| Composition E: Concentrated Solution | |
| Compound 5 | 90 |
| solvent (xylene) | 10 |
| Total | 100% |

What is claimed is:

1. A compound having the formula

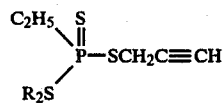

in which $R_2$ is 1,1-dimethylpropyl or 2,2-dimethylpropyl.

2. A compound according to claim 1 in which $R_2$ is 1,1-dimethylpropyl.

3. A compound according to claim 1 in which $R_2$ is 2,2-dimethylpropyl.

* * * * *